United States Patent [19]

Janski et al.

[11] Patent Number: 4,786,501
[45] Date of Patent: Nov. 22, 1988

[54] CYLINDRICAL IMPLANTS FOR THE CONTROLLED RELEASE OF GROWTH HORMONES

[75] Inventors: Alvin M. Janski; Ren-Der Yang, both of Terre Haute, Ind.

[73] Assignee: International Minerals & Chemical Corp., Terre Haute, Ind.

[21] Appl. No.: 755,093

[22] Filed: Jul. 15, 1985

[51] Int. Cl.$^4$ ............................................. A61S 3/00
[52] U.S. Cl. ................................... 424/422; 424/423; 424/424; 424/425; 424/426; 935/59; 935/60; 935/64; 514/964; 530/399; 530/412; 530/417
[58] Field of Search ............... 604/891, 892, 890, 896; 424/19, 31-33, 422-426; 935/60, 59, 64

[56] References Cited

U.S. PATENT DOCUMENTS

| | | | |
|---|---|---|---|
| 3,993,072 | 11/1976 | Zaffaroni | 424/422 |
| 4,158,526 | 5/1985 | Olson | 260/112 |
| 4,450,150 | 5/1984 | Sidman | 604/891 |
| 4,506,680 | 3/1985 | Stokes | 604/891 |
| 4,511,502 | 4/1985 | Builder et al. | 260/112 |
| 4,511,503 | 4/1985 | Olson et al. | 260/112 |
| 4,512,922 | 4/1985 | Jones et al. | 260/112 |
| 4,525,340 | 6/1985 | Lange et al. | 424/424 |
| 4,563,489 | 1/1986 | Urist | 604/891 |
| 4,576,604 | 3/1986 | Guittard et al. | 604/891 |
| 4,686,098 | 8/1987 | Kopchick et al. | 604/891 |

FOREIGN PATENT DOCUMENTS

| | | | |
|---|---|---|---|
| 0047600 | 3/1982 | European Pat. Off. | 935/60 |
| 0068646 | 1/1983 | European Pat. Off. | 935/60 |
| 8505377 | 12/1985 | PCT Int'l Appl. | |
| 2073245 | 10/1981 | United Kingdom | |

OTHER PUBLICATIONS

De Geeter et al, CA vol. 99, 1983, #157232u.
Blackshear, "Implantable Drug Delivery Systems" Scientific American 1979 pp. 66-73.

Primary Examiner—Howard E. Schain
Assistant Examiner—Garnette D. Draper
Attorney, Agent, or Firm—Wendell R. Guffey; Thomas L. Farquer

[57] ABSTRACT

This invention relates to a method for purifying and concentrating biologically active growth hormone to produce growth hormone in a form suitable for incorporation into a controlled release device (or system). A buffered solution of purified recombinant growth hormone is dialyzed against a buffered solution until the salt level is reduced to less than 5% and then lyophilized.

7 Claims, 1 Drawing Sheet

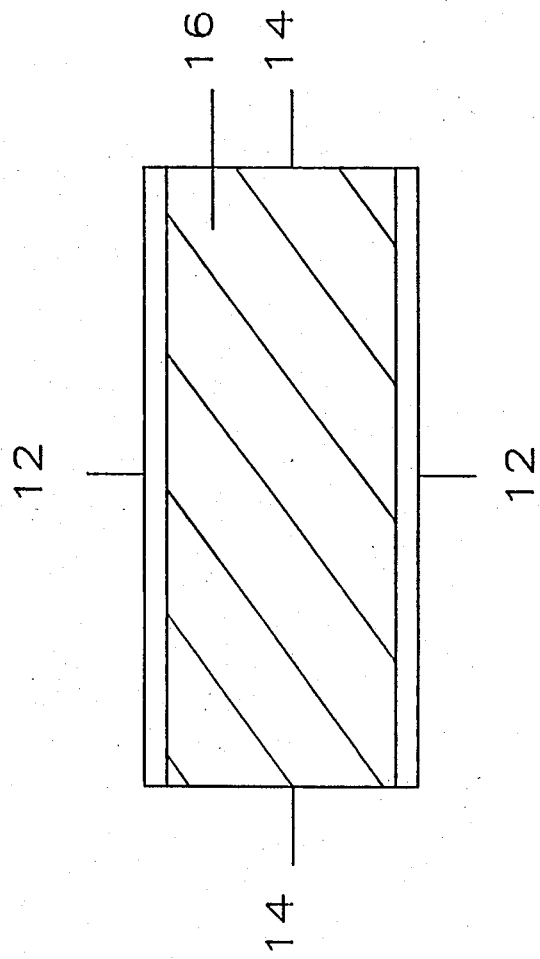

CYLINDRICAL IMPLANTS FOR THE CONTROLLED RELEASE OF GROWTH HORMONES

BACKGROUND OF THE INVENTION

The present invention relates to a method of producing controlled release implants adapted for the administration of bioactive recombinant growth hormones at a controlled and continuous rate to a host. More particularly, the invention relates to a method of purifying bovine growth hormone and porcine growth hormone produced by DNA technology in a form suitable for use in controlled release devices.

Growth hormones are proteins that are involved in regulating protein metabolism as well as fat, carbohydrate, and mineral metabolism. Growth hormones affect the metabolic processes of the body by increasing the rate of cellular protein synthesis and decreasing protein degradation, as well as by increasing the rate of use of fatty acids and decreasing the rate of use of carbohydrates for production of energy in the body.

Bovine growth hormone (BGH) and porcine growth hormone (PGH) are proteins containing 191 amino acid residues. These proteins are synthesized in the anterior pituitary gland as "pre-growth hormones" having 26 additional amino acid residues attached at the amino terminal end. These 26-amino acid residue sequences are cleaved off prior to secretion from the pituitary cells, yielding the mature hormones. Field trials using BGH purified from pituitary glands demonstrated increased milk production and improved feed-to-milk conversion in cows to which the hormone was administered (Machlin, L. J., *Journal of Dairy Science*, 56:575–580 [1973]). The potential economic value of this hormone sparked interest in obtaining BGH in commercial quantities at reasonable cost. Field trials of native PGH have shown increased growth rates in young swine receiving the hormone.

Thus, much work in recent years has focused on obtaining microbial synthesis of these commercially valuable hormones using recombinant DNA technology. Gene cloning and manipulation techniques, well known in the art, have been used to produce recombinant expression vectors capable of directing the synthesis of BGH and PGH. For example, microorganisms transformed with BGH-encoding cDNA linked to a regulatory system have been shown to produce the desired hormone. Keshet et al., (*Nucleic Acids Research*, 9:19–30 [1981]) reported the cloning and low level expression in *E. coli* of a full length BGH polypeptide as a fusion protein with a portion of pBR322-encoded β-lactamase. In European Patent Application Publication No. 0 103 395, construction of several expression vectors, including vectors encoding BGH polypeptides with varying portions of the aminoterminal end deleted, is described. BGH polypeptides with varying portions of the amino-terminal end of the mature hormone deleted were found to retain biological activity and to be expressed at much higher levels than was the complete hormone in the expression systems described.

Administration of BGH to cattle and PGH to swine has hitherto been only marginally successful. Methods of delivery of drugs that are well known in the art include oral, nasal, rectal, topical, and parenteral injection routes of administration. However, it is inconvenient to administer drugs to cattle and swine by these methods because of the large expense and amount of time required to deliver the drug to each member of a large group of animals on a daily basis.

Subcutaneous implants provide an alternative means for administering sustained, effective dosages of recombinant BGH and PGH to each animal. The implant contains a hormone reservoir surrounded by a protective wall permeable to the hormone. The advantage of these delivery systems is that they provide for controlled and predictable release rates of the hormones to the animals over an extended period of time. Unfortunately, we have found that controlled release devices containing BGH and PGH produced by recombinant microorganisms in fermentation media are subject to swelling and partial disintegration after implantation. This phenomenon dilutes the hormone in the implant and adversely affects the rate of release of the hormone. Therefore, the commercial need for a method of producing recombinant growth hormones in a form capable of effectively being incorporated into a controlled release implant persists.

SUMMARY OF THE INVENTION

The present invention relates to improved implants for the controlled and continuous administration of growth hormones to host animals. The implants are made of a compressed composition containing a growth-promoting amount of an animal growth hormone produced by recombinant DNA technology. More particularly, the present invention relates to a method of purifying and concentrating bovine growth hormone and porcine growth hormone produced by recombinant DNA technology in a form suitable for use in controlled release implants. A method of producing controlled release implants for administration of growth hormones into animals is also disclosed. The method of the invention is based on our discovery that reduction of the salt level of the growth hormones to less than 5% by weight eliminates the swelling problem previously encountered when recombinant growth hormones were incorporated into controlled-release implants. Unlike native growth hormone, the recombinant product contains a substantial amount of salt which is present largely as a result of salts in buffers used in the recovery operations.

In addition to removal of most of the salt, the present invention relates to a method for producing recombinant growth hormones in the presence of buffer salts that will result in a physiological pH of about 7.4 within the implant upon wetting in a physiological environment. This aspect of the invention prevents a pH gradient between the implant and its in vivo environment from developing. Such a gradient would cause uncontrolled release of growth hormone.

In accordance with the method of the invention, the animal growth hormone, which is recovered from transformant microorganisms in a fermentation medium, is dialyzed against a dialysis buffer having a pH from basic to physiological pH until the amount of salt present in the growth hormone is less than 5%. Methods other than dialysis for salt removal may provide for preparation of a low-salt product, e.g., size exclusion chromatography. The low-salt growth hormone thus produced is lyophilized and then admixed with a biocompatible polymer to produce a composition which can be compressed into a unitary dosage form capable of being subcutaneously implanted. The term "physiological pH" refers to a pH of about 7.4.

BRIEF DESCRIPTION OF THE DRAWING

The single FIGURE is a cross-sectional representation of a cylindrical implant for the controlled-release administration of growth hormone to an animal.

DETAILED DESCRIPTION OF THE INVENTION

We have developed a new method of producing growth hormones suitable for controlled release implants for administration to animals. More particularly, the invention provides a method of removing salts and concentrating bovine growth hormone or porcine growth hormone produced by recombinant DNA technology which results in a composition suitable for use in a controlled release implant for subcutaneous implantation. As used herein, the terms "bovine growth hormone", "BGH", "porcine growth hormone", and "PGH" include fragments of the hormones which may, for example, have varying portions of the amino terminal ends of the hormones deleted, or may have various substitutions or modifications in the BGH and PGH sequences which do not destroy the biological activity of the polypeptides. BGH and PGH polypeptides lacking various portions of the amino terminal end of the hormones have been shown to retain biological activity.

The cloning and microbial expression of the BGH and PGH genes can be carried out using conventional techniques of molecular biology. The plasmids that direct the expression of BGH and PGH in transformed microorganisms can be any suitable growth hormone-encoding plasmids. The host microorganisms may be either Gram-positive or Gram-negative. Gram-negative microorganisms include those selected from the genus Escherichia. Gram-positive microorganisms include those selected from the genus Bacillus and the genus Streptomyces. The precise host microorganism employed is not critical.

In producing the BGH used in the process of the invention, we employed an *E. coli* host strain HB101 or MC1061 transformed with a first plasmid, pL-mu-$\Delta$ 9C143, coding for bovine growth hormone less its nine N-terminal amino acids and having a codon for serine at the N-terminal end, under the control of phage lambda promoter and a second plasmid, pCI857, which codes for the temperature sensitive phage lambda repressor protein. Construction of a transformant strain of this type is described in detail in European Patent Application Publication No. 0 103 395. The HB101 transformant strain, identified as *E. coli* IMC No. 1, has been deposited at the American Type Culture Collection, Rockville, Maryland with accession no. ATCC 53030. Applicants have directed that the deposited microorganism be freely available to the general public upon issuance of a U.S. Patent. It will be readily apparent, however, that the process of this invention is equally applicable to the purification of recombinant BGH produced by any host/vector combination.

For the production of PGH, we employed an *E. coli* host strain HB101 transformed with a first plasmid, $P_L$-mu-$\Delta$ 7 SGH, coding for porcine growth hormone less its seven N-terminal amino acids under the control of phage lambda promoter and a second plasmid pCI857, which encoded a temperature-sensitive repressor used to control PGH in the method of the invention. This transformant strain, identified as *E. coli* IMC No. 2, has been deposited at the American Type Culture Collection, Rockville, Maryland with accession no. 53031. Applicants have directed that the deposited microorganism be freely available to the general public upon issuance of a U.S. Patent.

Following the expression in microbial culture of the cloned recombinant BGH or PGH gene, preparations of growth hormone may be recovered using various techniques of preliminary fractionation. When a sufficient amount of the recombinant BGH or PGH has been expressed by the transformed microorganisms, the cells are separated from the bulk of the culture medium, normally by centrifugation. The expressed protein is then obtained from the cells, in the case of a non-secreting host such as *E. coli,* or from the medium, in the case of a secreting host such as *B. subtilis*. In the case of a non-secreting host such as *E. coli,* the cells must be disrupted in order to release the protein. Disruption can be achieved mechanically using, for example, a French press or a Manton-Gaulin homogenizer, and the cell debris removed, or it can be achieved chemically. The composition which is subjected to the purification process of the invention may contain—in addition to the microbially produced protein—other proteins which are expressed by the transformant host microorganism, residual structural proteins of the host microorganism, microbial metabolites including endotoxins, residual constituents of the fermentation medium and any other residual materials resulting from fermentation and expression. Upon completion of the cell disruption, the BGH or PGH may then be separated from the cell debris and the impurities by methods such as centrifugation, large scale chromatography, and batch extraction techniques.

As previously indicated, the steps of the recovery procedure of this invention involve dialysis of the recombinant BGH or PGH followed by lyophilization. As used herein, the term "dialysis" refers to any technique in which salt is removed from the growth hormone solution by selective transport of salt ions across a semi-permeable membrane with retention of the desired growth hormone molecules on the other side of the membrane. Any of the known methods of dialysis may be used with a variety of types of equipment. For example, small molecules in a protein solution may be dialyzed or ultrafiltered using hollow fiber ultrafiltration systems. In this procedure, dialysis buffer solution of low ionic strength is passed through bundles of semipermeable hollow fibers. Small molecules in the protein solution that surrounds the fibers are capable of passing through the membranous fiber wall so as to reduce the ionic strength of the protein solution.

A convenient dialysis technique for small scale dialysis involves adding the recombinant BGH preparation to a buffer solution and placing this mixture into a sac made by knotting each end of a semipermeable dialysis tubing. The sealed tubing containing the BGH is dialyzed against increasingly lower concentrations of buffer until the BGH is at least 95% salt free. The buffer preferably does not contain sodium chloride. The pH of the dialysis buffer solution is maintained within the range of 9.6 to 10.0, preferably 9.8. The temperature is generally maintained within the range of 5° to 15° C. A particularly useful buffer is sodium bicarbonate/sodium carbonate of the composition 25 mM $NaHCO_3$, 21 mM $Na_2CO_3$. This buffer has been called "Cornell Buffer minus sodium chloride" and it is designated by the symbol $CB^-$. The BGH may be dialyzed directly from concentrated buffer into dilute buffer or may be dialyzed by stepwise dialysis into the dilute buffer from less dilute buffer. These procedures are effective for removing salt and lowering the ionic strength.

In a procedure which is useful for processing BGH on a larger scale, a purified dilute solution of BGH (generally less than 1.0 mg/ml) is concentrated to greater than 1.0 mg/ml in a cross-flow membrane filtration unit (such as an Amicon DC-10 unit) using a membrane that will pass most of those molecules having a molecular weight of less than 10,000. The resulting concentrated product solution in 60 mM ethanolamine buffer at pH 9.0 is diafiltered using the same membrane unit against 2 volumes of 50% strength CB$^-$ and then 5 volumes of 2% strength CB$^-$. The resulting product retentate, now in 2% CB$^-$ buffer, is then further concentrated to final product concentrates of between 5-20 mg/ml. Before lyophilization, the final concentrate is clarified by centrifugation followed by 0.2 $\mu$ microporous filtration.

The procedures described above generally achieve a recovery efficiency of between 60 to 80% with the resulting lyophilized product containing less than 5% salts (pH 9.8).

In the lyophilization step, a solution of BGH is placed in shallow trays that are then put on the shelves in a high-vacuum chamber. The shelves are maintained by refrigeration at a temperature of about $-40°$ C. during freezing. During sublimation of water substance, the shelf temperature is maintained at approximately 25° C.

After each step of the purification procedure, identification of the recombinant growth hormone product may be confirmed by any suitable means. A convenient procedure involves resolubilization of the product followed by Bio-Rad protein assay and radio receptor assay.

Porcine growth hormone may be recovered by the foregoing method used for BGH. However, a preferred method for PGH entails dialyzing the PGH preparation against a buffer having a physiological pH of about 7.4. This buffer has the following composition:

2-5 mM Tris
pH=7.4 adjusted with HCl
Tris=(Tris(hydroxymethyl)amino-methane).

In a preferred procedure for processing PGH, a purified dilute solution of PGH (generally less than 1.0 mg/ml) is concentrated to greater than 1.0 mg/ml in a cross-flow membrane filtration unit (such as an Amicon DC-10 unit) using a membrane that will pass most molecules having a molecular weight of less than 10,000. The resulting concentrated product solution in 60 mM ethanolamine buffer at pH 9.0 is diafiltered using the same membrane unit against 5 volumes of Tris buffer at 2-5 mM concentration and pH 7.4.

The resulting product retentate, now in 2-5 mM Tris buffer, is then further concentrated to final concentrations of between 5 and 20 mg/ml. Before lyophilization, the final concentrate is clarified by centrifugation followed by 0.2 $\mu$ microporous filtration.

The procedures described produce a final lyophilized product with less than 5% salts at pH 7.4. The recovery yield is comparable to CB$^-$ buffer finishing for PGH but lower for BGH.

After dialysis, the PGH solution is lyophilized as described for BGH.

Either the lyophilized BGH or PGH may be incorporated in an implant for subcutaneous administration as described in the following paragraphs.

For the controlled administration of growth hormone (GH) from solid implants, it is advantageous to have a matrix consisting of the GH, a polymer as a filler and other suitable additives. It is important that the polymeric filler be biocompatible and compatible with the GH. For example, if the polymer is too hydrophobic, it may bind the GH so strongly that the protein may not be released readily. In extreme cases, the GH may even be denatured by the hydrophobic matrix and thus rendered inactive. On the other hand, if the polymer is too hydrophilic, penetration of water into the implant can be rapid. The wet implant may facilitate aggregation of the GH which can result in decreased solubility and/or bioactivity. Thus, the ideal polymeric filler should exhibit a balance between the hydrophobic and hydrophilic forces.

Ethyl cellulose (EC) is a commercially available, water-insoluble polymer which fits the requirements of a polymeric filler for an implant containing GH. It is a derivative of cellulose in which the hydroxyl groups have been partially etherified. The ether groups provide the hydrophobicity while the hydroxyl groups give hydrophilicity to the polymer. By altering the degree of etherification, one can achieve the desired balance between the two types of interaction. Another advantage of EC is the presence of the unsubstituted hydroxyl groups which may stabilize the GH in the wet implant and minimize aggregation of the protein. A third advantage is the ability of EC to act as binder in tablet preparations. By controlling the amount of the EC in the matrix, it is possible to control the compactness of the solid pellet. This can be used to control the water penetration into the implant and the disintegration of the pellet.

GH, being a delicate protein, may easily be denatured when brought into contact with organic solvents. In conventional tablet formulations, the drug is usually mixed with a solution of the polymeric filler, dried and granulated. This may not be desirable for the formulation of GH as a solid implant. EC offers another advantage in that it can be formulated in the dry state with the GH, thus avoiding the potentially damaging exposure to organic solvents.

In summary, EC can be very useful in the formulation of a solid implant containing GH. The amount of EC can vary from 10 to 50% depending on the type of release profile needed. It can also be used in conjunction with other suitable additives such as sucrose, lactose, magnesium stearate, etc. which are employed in conventional tablet formulation for various purposes.

Referring to the single Figure, a typical controlled release implant incorporating BGH can be produced as follows. BGH (75 parts; particle size: 150-250 microns) and EC (25 parts; particle size: 150-250 microns) are mixed in a vial using a vortex shaker. The matrix is then pelleted with a Stoke's machine to give cylindrical pellets weighing 50 mg and measuring 4.0 mm in diameter and 3.9 mm in length. The pellets are placed in microporous polyethylene (MPE) tubes and the ends of the tubes sealed with non-porous polyethylene film. The resultant cylindrical implant for the controlled release of GH is illustrated in cross-section in the single Figure. The cylindrical implant contains a central core pellet 10 which is surrounded along the length of the cylinder by a releasing surface 12 of the microporous polyethylene film. At the end or the cylinder are nonreleasing surfaces 14 of non-porous polyethylene.

Upon subcutaneous implantation in cattle, the releasing surface 12 of MPE acts as a barrier to slow the rate of diffusion of BGH out of the implant, thereby resulting in a prolonged release of the hormone. If desired, other microporous polymer films may be used in place of the MPE. These include, for example, microporous films of ethyl cellulose, polycaprolactone and polymethyl methacrylate. The non-releasing surface 14 of non-porous polyethylene (or other non-porous polymer) serves to prevent BGH from being released through the ends of the implant.

The following examples will serve further to illustrate this invention without limiting the invention thereto.

EXAMPLE 1

Δ9 BGH was obtained by lysis of *E. coli* (MC1061) transformant cells which had been grown in a fermentation medium at 28° C. until the $A_{550}$ of the medium reached 50-60 and then induced to express BGH oy raising the temperature to 42° C. After removal of unwanted cellular material and recovery by conventional techniques of protein solubilization and purification, there was obtained 1500 ml of aqueous solution of Δ9 BGH at a concentration of 110 ppm. This solution was concentrated to 350 ml by ultrafiltration across a membrane which passed molecules below 5,000 molecular weight. The solution was clarified by centrifugation and the supernatant was concentrated to 32 ml by ultrafiltration. The solution was then dialyzed by sack dialysis against approximately 320 ml of CB$^-$ buffer (25 mM NaHCO$_3$, 21 mM Na$_2$CO$_3$, pH 9.8). The solution was concentrated to 6.2 ml by ultrafiltration across a membrane which passed molecules below 10,000 molecular weight. The solution was clarified by centrifugation and filtration through a 0.2 μ microporous filter to give 6.2 ml having a protein concentration of 11.4 mg/ml. The preparation was diluted to about 2 mg/ml in 1×CB$^-$ and a 10 ml sample was dialyzed overnight in a Spectropore 1 (6,000-8,000 Dalton cutoff) tubing against 1,600 ml 1×CB$^-$, pH 9.67. The product was further dialyzed to remove salt as follows:

A one milliliter sample of the product was stepwise dialyzed against 0.2×CB$^-$ for 4 hours, then 0.05×CB$^-$ for 4 hours, and finally 0.01×CB$^-$ overnight. Another one milliliter sample of the product was directly dialyzed against 0.01×CB$^-$. After dialysis, each bag was mixed by inversion.

One ml aliquots were removed from each dialysis bag and transferred to separate silanated glass liquid-scintillation vials. The samples were shell-frozen in dry ice-acetone and lyophilized overnight at about 7 microns Hg pressure.

After each dialysis, and following lyophilization, samples of the product were solubilized in phosphate buffered saline (10 mM Na$_2$HPO$_4$, 10 mM NaH$_2$PO$_4$, 140 mM NaCl, pH 7.4), and the purity of the product was determined by Bio-Rad protein assay and radio receptor assay. The radio receptor assay, as described by J. Roth, *Methods in Enzymology*, 37 (1975), 66-81 (Chapter 4), is a competitive binding assay in which the test sample containing BGH and a sample of known concentration of $^{125}$I-labelled BGH are incubated with a suspension of small particulate vesicles of pregnant rabbit liver membrane growth hormone receptors. Bound label is separated from unbound label by centrifugation and the centrifugation pellet containing the bound label is placed in a gamma counter. The BGH titer in the sample was determined by comparison with a standard curve. The results of solubility and radio receptor assay experiments are presented in Table 1 for the samples which were dialyzed directly or in stepwise fashion, as well as for samples which did not undergo dialysis. Dialysis, lyophilization, and resolubilization in phosphate buffered saline of Δ9 BGH led to retention of over 92% of the hormone's solubility, 95% recovery of the hormone, and retention of radio receptor binding activity.

TABLE 1

| Dialysis Process | Final Buffer | Solubility After Dialysis (%) | Recovery After Dialysis (%) | Solubility in PBS After Lyophilization (%) | Recovery After Lyophilization (%) | Radioreceptor Assay Activity (±) |
|---|---|---|---|---|---|---|
| None | 1 XCB$^-$ | 99.2 | 95.0 | N/A | N/A | + |
| Stepwise | 0.01 XCB$^-$ | 96.7 | 98.9 | 102 | 95.1 | + |
| Direct | 0.01 XCB$^-$ | 105 | 105 | 92.8 | 100 | + |

EXAMPLE 2

One hundred liters of purified Δ9 BGH at a concentration of approximately 150 mg/L in 60 mM ethanolamine buffer was obtained from *E. coli* IMC No. 1 cells (ATCC 53030) which had been grown in a fermentation medium. The solution was concentrated to about 2100 mg/L in a cross-flow membrane filtration unit (e.g., Amicon DC-10) equipped with a membrane that passes most of those molecules with molecular weights below 10,000. The resulting concentrated product solution in the 60 mM ethanolamine buffer at pH 9.0 was diafiltered against a 2×volume of 50% strength CB$^-$ buffer and then 5 volumes of 2% CB$^-$ buffer. The resulting retenlate, now in 2% CB$^-$ buffer, was then further concentrated in an Amicon DC-10 unit to a final value of 14 mg/mL. Before lyophilization, the final concentrate is clarified by centrifugation and filtration through a 0.2 micron microporous filter.

The filtered solution was lyophilized to give a product that contains less than 5% salts and gives a solution with a pH of 9.8 when added to deionized water.

The procedure described above gave a yield of about 90%; however, more typical yields are 60-80%.

EXAMPLE 3

Sixty-three liters of purified Δ7 PGH at a concentration of approximately 80 mg/L in 60 mM ethanolamine buffer was obtained from *E. coli* IMC No. 2 cells (ATCC 53031) which had been grown in a fermentation medium. The solution was concentrated to about 800 mg/L in a cross-flow membrane filtration unit (e.g., Amicon DC-10) equipped with a membrane that passes most of those molecules with molecular weights below 10,000. The resulting concentrated product solution in the 60 mM ethanolamine buffer at pH 9.0 was diafiltered against a 5×volume of Tris.HCl buffer at 2-5 mM concentration and a pH of 7.4. The resulting product retentate, now in 2-5 mM Tris buffer, was then further concentrated in an Amicon DC-10 unit to a final value of from 2.5 to 20 mg/mL. Before lyophilization, the final concentrate is clarified by centrifugation and filtration through a 0.2 micron microporous filter.

The filtered solution was lyophilized to give a product that contains less than 5% salts and gives a solution with a pH of 7.4 when added to deionized water.

When an implant of PGH in the presence of pH 7.4 buffer salts is wetted by body fluids at about pH 7.4, little or no pH gradient should exist, allowing for a more predictable release rate of PGH from the implant.

The procedure described above gave a yield of at least 60%.

EXAMPLE 4

A formuation for the preparation of growth hormone implants is prepared from the following ingredients:

| Ingredient | Parts by Weight |
|---|---|
| BGH or PGH | 30 |
| Sucrose | 40 |
| Ethyl cellulose | 30 |

The ingredients are mixed in a vial using a vortex shaker. The mixture is pelleted using a Stoke's machine to give cylindrical pellets weighing 50 mg and measuring 4.0 mm in diameter and 3.9 mm in length. The pellets are placed in microporous polyethylene tubes and the ends are sealed with non-porous polyethylene.

What is claimed is:

1. A cylindrical implant for the controlled and continuous administration of growth hormone to a host comprising a compressed composition of an animal growth hormone produced by expression of a gene coding for the hormone in a transformant microorganism, said growth hormone being recovered from said microorganism and processed to produce a growth hormone containing less than 5% salt, and a biocompatible and growth hormone compatible polymer, said composition being surrounded along the length of the cylinder by a microporous polymer film and sealed at its ends by a non-porous polymer film.

2. The implant of claim 1 wherein the growth hormone is selected from bovine growth hormone and porcine growth hormone.

3. The implant of claim 2 wherein the compatible polymer is ethyl cellulose.

4. The implant of claim 2 wherein the compressed compostion contains about 30 weight percent growth hormone, 30 weight percent ethyl cellulose and 40 weight percent sucrose.

5. The implant of claim 2 wherein the microporous polymer is microporous polyethylene and the non-porous polymer is non-porous polyethylene.

6. The implant of claim 1 wherein the compressed composition contains from about 50-90 weight percent growth hormone and from about 10-50 weight percent biocompatible and growth hormone compatible polymer.

7. The implant of claim 6 wherein the biocompatible and growth hormone compatible polymer is ethylcellulose, the microporous polymer is microporous polyethylene and the non-porous polymer is non-porous polyethylene.

* * * * *

UNITED STATES PATENT AND TRADEMARK OFFICE

Certificate

Patent No. 4,786,501                                          Patented: November 22, 1988

On petition requesting issuance of a certificate for correction of inventorship pursuant to 35 USC 256, it has been found that the above-identified patent, through error and without any deceptive intent, improperly sets forth the inventorship. Accordingly, it is hereby certified that the correct inventorship of this patent is:

Alvin M. Janski
                               Ren-Der Yang
                               Kallidaikurichi N. Sivaramakrishnan Signed and Sealed this Twenty-Second Day of August, 1989

MARGARET MOSKOWITZ
                                                                                            *SPE, Art Unit 186*

UNITED STATES PATENT AND TRADEMARK OFFICE
CERTIFICATE OF CORRECTION

PATENT NO. : 4,786,501
DATED : November 22, 1988
INVENTOR(S) : Alvin M. Janski et al.

It is certified that error appears in the above-identified patent and that said Letters Patent is hereby corrected as shown below:

Column 7, line 4, "celluIose" should read --cellulose--

Column 7, line 26, "oy" should read --by--

Column 8, line 42, "retenlate" should read --retentate--

Column 9, line 14, "formuation" should read --formulation--

Column 10, Claim 4, line 2, "compostion" should read --composition--

Signed and Sealed this

Thirty-first Day of October, 1989

Attest:

DONALD J. QUIGG

Attesting Officer

Commissioner of Patents and Trademarks